United States Patent [19]

Krause et al.

[11] Patent Number: 4,498,944
[45] Date of Patent: Feb. 12, 1985

[54] METHOD AND APPARATUS FOR PRODUCING AN ELASTICIZED GARMENT BY TUCKING A PORTION OF THE DIAPER WEB DURING BONDING OF ELASTIC TO THE UNTUCKED PORTIONS OF THE WEB

[75] Inventors: Charles E. Krause; William J. Moore, both of Appleton, Wis.

[73] Assignee: Kimberly-Clark Corporation, Neenah, Wis.

[21] Appl. No.: 340,543

[22] Filed: Jan. 18, 1982

[51] Int. Cl.³ ............................................. B32B 31/08
[52] U.S. Cl. ..................................... 156/205; 156/164; 156/229; 156/292; 156/469; 156/470; 156/471; 156/474; 156/495; 156/554; 156/560; 425/336; 425/369; 425/370; 425/396
[58] Field of Search ............... 156/204, 205, 164, 229, 156/469, 470, 471, 474, 495, 292, 554, 560; 425/336, 370, 369, 396

[56] References Cited

U.S. PATENT DOCUMENTS

| 1,284,771 | 11/1918 | Quinn | 425/369 |
| 2,514,801 | 7/1950 | Sapp | 425/370 |
| 3,102,776 | 9/1963 | Steinmann et al. | 425/396 |
| 3,311,524 | 3/1967 | Hecker | 156/471 |
| 3,792,952 | 2/1974 | Hamon | 425/336 |
| 4,227,952 | 10/1980 | Sabee | 156/164 |

Primary Examiner—Jerome Massie
Attorney, Agent, or Firm—Howard Olevsky

[57] ABSTRACT

An apparatus and method is disclosed for attaching a continuously moving elastic ribbon to a continuously moving web such that only selected discrete areas of a finished conformable garment fabricated from the web are elasticized. The web is moved into engagement with a continuously moving first conveyor means having a plurality of spaced apart gaps in its surface and the first conveyor means travels along an inclined guide means toward a second conveyor means traveling opposite to and in the same direction as the first conveyor means. The second conveyor means carries a plurality of spaced apart web tucking means which are moved by the second conveyor means into registry with the gaps in the first conveyor means. As each of the web tuck means move in registry with the gaps, the web tuck means are inserted into the gaps to form tucks in the web due to the movement of the first conveyor means toward the second conveyor means. After forming of the tucks in the web, the continuously moving elastic ribbon is applied to the web such that it spans the tucks and adheres to the area of the web between the tucks. The elastic ribbon is then cut opposite the tuck locations of the web and the tucks are removed from the web.

8 Claims, 6 Drawing Figures

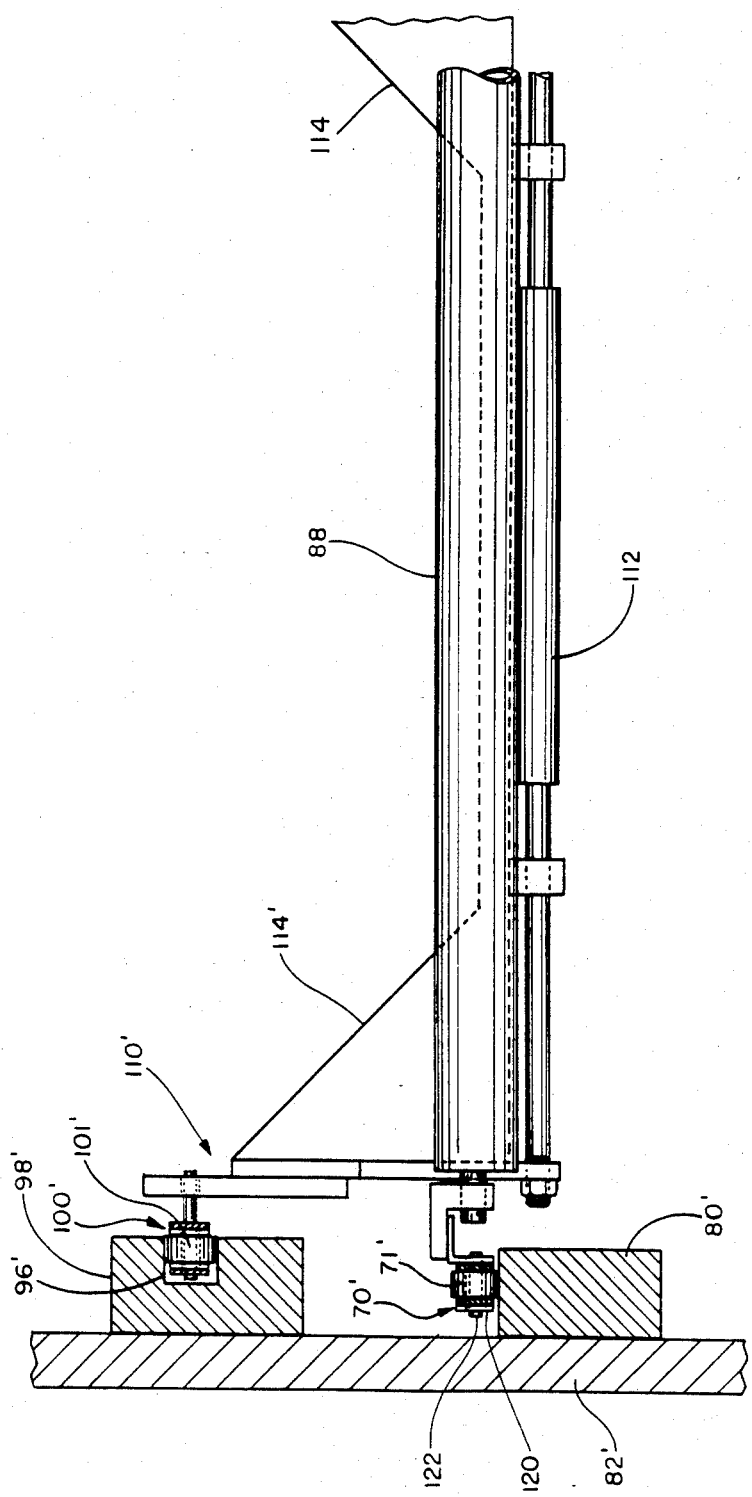

METHOD AND APPARATUS FOR PRODUCING AN ELASTICIZED GARMENT BY TUCKING A PORTION OF THE DIAPER WEB DURING BONDING OF ELASTIC TO THE UNTUCKED PORTIONS OF THE WEB

FIELD OF THE INVENTION

This invention relates to an apparatus and method for forming conformable garments having selected discrete elasticized areas and, more particularly, to an apparatus and method for elasticizing only the leg areas of disposable diapers on a high speed production basis.

BACKGROUND OF THE INVENTION

Due to the improved fit and fluid sealing properties provided by leg elasticization, manufacturers of disposable diapers have, in recent years, developed various methods and apparatus for attaching elastic strips to the leg areas of the diapers. Because of the high speed, continuous nature of diaper manufacturing methods, virtually all of the commercially practicable processes have utilized a continuous elastic ribbon affixed to the diaper in the leg areas and subsequently cut either prior to or as a part of the severing of the continuous web into separate diapers. Typical of these processes and apparatus is that disclosed in U.S. Pat. No. 4,081,301 to Buell. This patent discloses adhering of the continuous elastic ribbon only in discrete, intermittent areas corresponding to the leg areas in a finished diaper. After adhering of the ribbon to a continuous web, the ribbon and the web are simultaneously cut at what will be the waist of the diaper when the manufacturing process is finished. The drawback of this process is that it is inefficient from the material use aspect in that it leaves an unneeded length of elastic attached to the diaper. Another approach to handling the problem is disclosed in U.S. Pat. No. 4,227,952 to Sabee. In the method of this patent, the elastic ribbon is continuously applied to the web, however, before the attachment of the ribbon to the web, the latter is tucked in the areas of the web corresponding to the waist areas of the finished diapers. Consequently, the elastic ribbon is attached to the web only in the leg areas of the finished diaper. The elastic ribbon is then severed at the points opposite the tucked areas of the web and the web is then untucked so that elastic is only in the leg areas of the finished diaper and the waist areas contain no unneeded elastic. The problem with this method and the apparatus used in it is that it is difficult to operate at the high speeds required for commercial usefulness. Much of the difficulty of the Sabee approach is due to the attempt to intermesh, in gear wheel fashion, projecting tucking members with members defining receptacles to form tucks in the web. Intermeshing of these members in this manner is too abrupt and presents positioning difficulties which prevent high speed operation and places too much stress on the web. Also, the depth of the tuck is limited by the width of the receptacles openings through which the tucking members must rotate to form the tucks.

A second approach using a tucking method is that disclosed in U.S. application Ser. No. 181,821, filed Aug. 27, 1980, now abandoned. The apparatus and method of this application solves the intermeshing difficulties of Sabee by mounting the projecting tucking members on a conveyor chain in a manner such that they are moveable relative to the conveyor chain in the direction of their length. The movement of the tucker members into the tuck defining receptacles is caused by cam means connected to the tucker members so that the rate of insertion of the tucker members into receptacles and the position at which they are inserted is controlled relatively independently of the position and movement of the conveyor chain carrying the tucker members. However, this approach has the problems of considerable complexity resulting in high initial cost of the apparatus and substantial wear requiring constant maintenance and adding further to the overall cost.

It is a principal object of this invention to provide, for use in a high speed production process and apparatus, a relatively simple, efficient method and apparatus for attaching a continuously moving elastic ribbon to a continuously moving web such that only selected discrete areas of a finished conformable garment fabricated from the web will be elasticized. The conformable garment may be a disposable diaper in which only the areas of the web corresponding to the leg areas in finished diapers will be elasticized. It is a particular object of this invention to provide a method and apparatus for forming tucks in a continuously moving web utilizing a relatively simple apparatus and method which facilitates and positions the forming of the tucks to permit their forming at high speed.

The objectives of the invention are accomplished by providing a first continuously moving conveyor means having a supporting surface with spaced apart gaps therein on to which a web is continuously moved and a second continuously moving conveyor means carrying a plurality of tucker bars rigidly mounted on and extending from the second conveyor means and inserted into and removed from the gaps of the first conveyor means as the two conveyor means move opposite each other in the same direction. The first conveyor means includes a pair of endless conveyor chains having a plurality of groups of spaced apart pairs of rollers with the rollers of each pair spaced apart to define the aforementioned gaps. A plurality of bars are disposed between each pair of rollers and form said supporting surface. The first and second conveyor means are moved along paths such that, during a portion of their movement along the paths, each tucker bar extending from the second conveyor means is in registry with the gaps of the first conveyor means. While the tucker bars are in registry with the gaps and the two conveyor means are moving in the same direction, the first conveyor means is directed, at the feed end of the apparatus, toward the second conveyor means and the tucker bars at a relatively gradual rate by a guide means such that the tucker bars are inserted into the gaps to form tucks in the web. During the insertion movement the tucker bars are rigidly carried by the second conveyor means at a substantially constant angle such that the insertion of the tucker bars into the gaps and the extent of this insertion is due largely to the movement of the two conveyor means toward each other rather than the rotation of the tucker bars or their movement relative to the second conveyor means.

After the tucker bars are inserted to the maximum depth in the gaps to complete the tucks, the elastic ribbons are brought into contact with the web so that the elastic spans the tucks and engages only the areas of the web between the tucks. The elastic ribbons are then cut opposite the tucks and the first conveyor means is guided away from the second conveyor means so that the tucker bars are withdrawn from the gaps. As the web leaves the apparatus at its exit end, the speed of movement of the web is increased to remove the tucks.

DESCRIPTION OF THE DRAWINGS

Further objects and advantages of the invention will appear when taken in conjunction with the accompanying drawings in which:

FIG. 6 is a cross-sectional view of the apparatus of the invention taken along the lines 6—6 of FIG. 5.

DETAILED DESCRIPTION OF THE INVENTION

Figure 1:
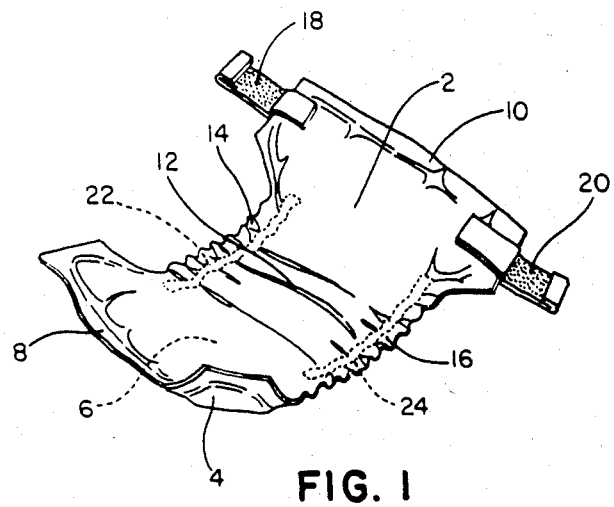
FIG. 1 is a perspective view of a finished elasticized leg disposable diaper just prior to its fitting onto a wearer.
Figure 2:
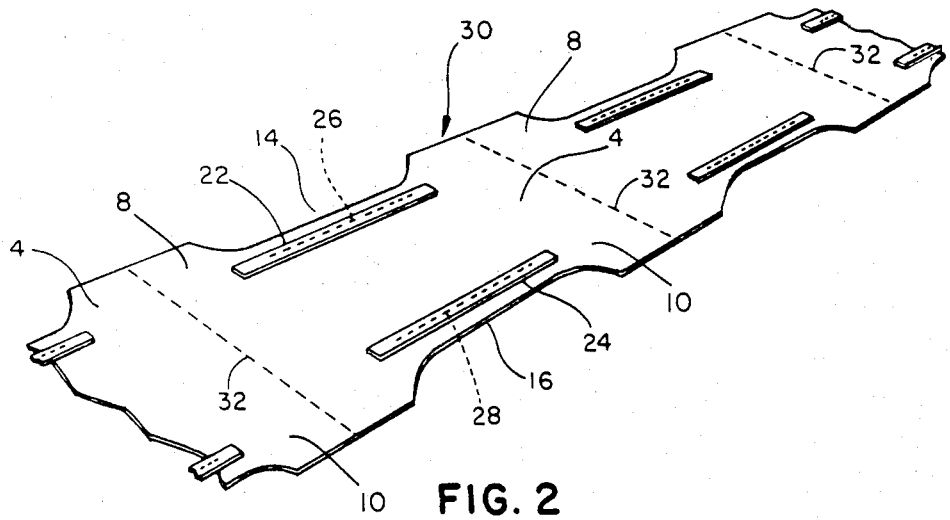
FIG. 2 is a perspective view of a diaper backsheet after the elastic ribbons have been applied for providing leg elasticization.

For purposes of background, the elasticized leg disposable diaper produced by the apparatus and method of the invention will first be discussed. Referring to FIGS. 1 and 2, there is shown in FIG. 1 a disposable diaper having a topsheet 2 and the backsheet 4, a front waist area 8, a rear waist area 10, and a crotch area 12 intermediate the two waist areas. Leg areas 14 and 16 are positioned laterally of the crotch area 12 and intermediate of the waist areas 8 and 10. Waist fastening tapes 18 and 20 are bonded to the corner areas of the rear waist area 10 and are fastenable to the front waist area 8 when the diaper is fitted to a wearer to secure the diaper on the wearer. Elastic strips 22 and 24 are attached substantially parallel to the length of a diaper in the leg areas 14 and 16 respectively, as shown in FIG. 2, to elasticize the leg areas of the diaper and provide a snug fit around the legs of the wearer. In FIG. 1, the elastic strips 22 and 24 are shown in a relaxed condition in which they cause random pleating or folding of the topsheet 2 and backsheet 4.

In FIG. 2, a web 30 is shown with the backsheet 4 of each diaper which is eventually cut from the web 30 being separately identified by the dashed lines 32. Attached to each backsheet 4, by adhesive lines 26 and 28, respectively, are elastic strips 22 and 24. The backsheet 4 and the elastic strips 22 and 24 are shown in an extended, flat condition in which the elastic strips 22 and 24 are stretched. The leg areas 14 and 16 have previously been cut from the web.

With reference to FIGS. 3-6, an apparatus is shown for supplying the web 30 to a web supply section 38, tucking or folding the web 30 at a tucking section 40, supplying and attaching elastic ribbons 34 to the web 30 at section 42, cutting the elastic ribbons 34 opposite the location of the tucks 36 at the cutting section 44, and untucking the web 30. Apparatus for applying the absorbent pads 6, the waist fastening tapes 18 and 20, and the topsheet 2, all illustrated in FIG. 1, is not shown or described herein inasmuch as they form no part of the present invention and may be incorporated into the finished diaper by methods and apparatus that are well known in the art.

Figure 3:
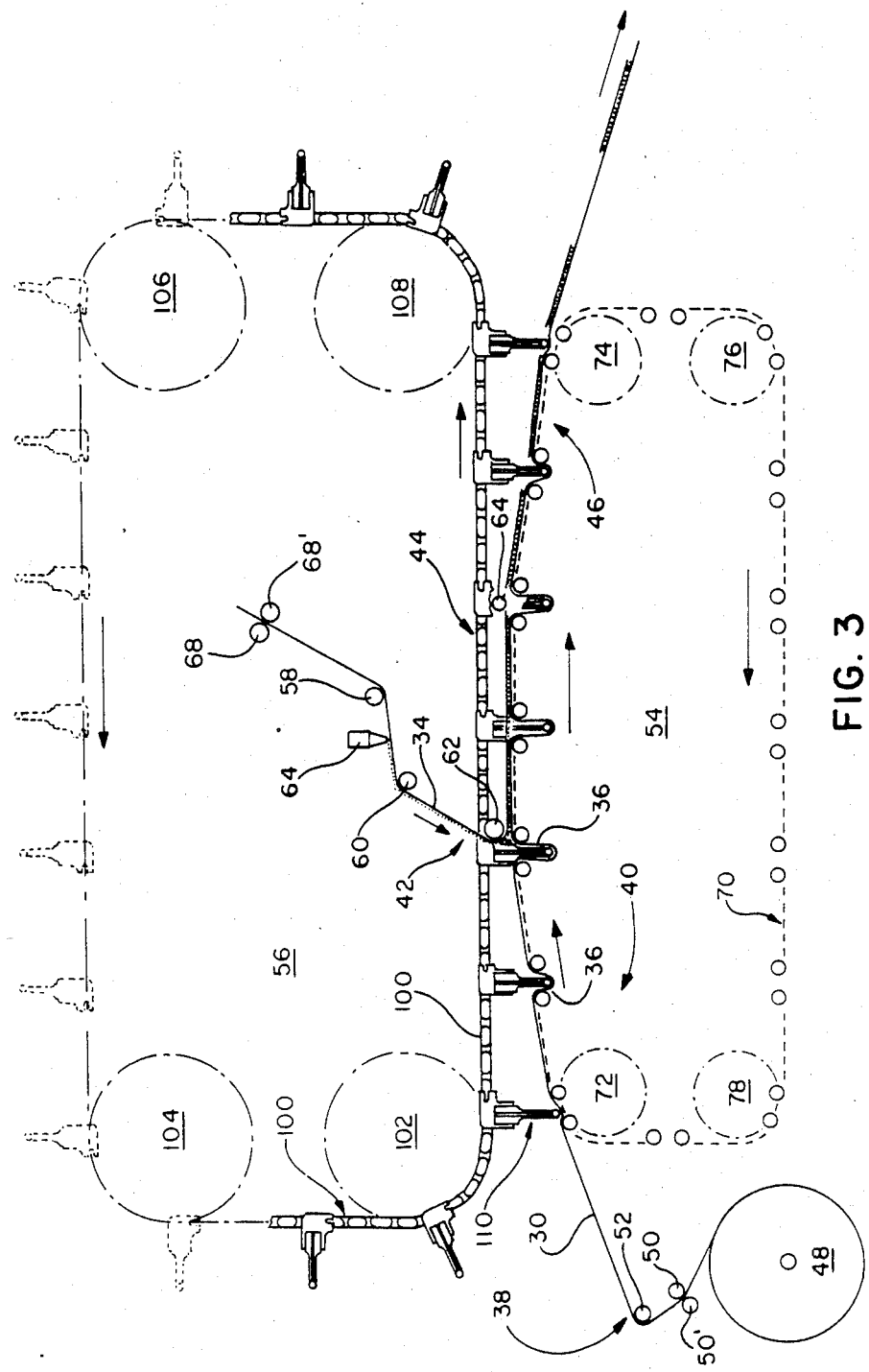
FIG. 3 is a simplified side elevation, cross-sectional view showing the two conveyors, the web supply, elastic supply, web tucking, elastic attaching, elastic cutting, and tuck removal stations of the diaper manufacturing apparatus of the invention.

With reference to FIG. 3, at the web supply section 38, the web material 30 is drawn from a supply roll 48 by feed rolls 50, 50' and, after passing over tension roll 52, the web 30 is fed to the tucking section 40 at the feed end of the apparatus where tucks 36 are formed in the web 30 by the intermeshing action of the first conveyor means 54 and the second conveyor means 56. At the elastic ribbon supply and application section 42, the elastic ribbons 34 are drawn from supply rolls (not shown) by feed roll means 68, 68'. The elastic ribbons 34 are then passed between tension sensing roll means 58 and 60 and under nip roll means 62 as they are applied to the web 30.

A feedback means (not shown), controls the speed of the feed roll means 68, 68' such that the elastic ribbons 34 are applied to the web 30 under tension. The effect of applying the elastic ribbons under tension is to elasticize those portions of the diapers obtained from the web when the web is cut and the cut members are in a relaxed condition. Prior to application of the elastic ribbons 34 to the web 30, adhesive applicator means 64 applies at least one line of adhesive to each of the ribbons 34 to permit adhering of the ribbons 34 to the web 30 as they pass under the nip roll means 62. Note, however, that other materials and methods or means may be used to bond or adhere the elastic ribbons 34 to the web 30. For example, energy may be applied to the ribbons 34 to cause their bonding to the web 30 or the ribbons 34 may be of an elastic material which itself adheres to the web 30.

The ribbons 34 are then cut opposite the tucks 36 in the web 30 by a cutter 64 at the ribbon cutting section 44 and the tucks 36 are then removed at the untucking section 46 at the exit end of the apparatus. The continuous web 30 with the spaced apart elastic strips 22 and 24, as shown in FIG. 2, then continues on to additional sections in the diaper producing apparatus.

Figure 4:
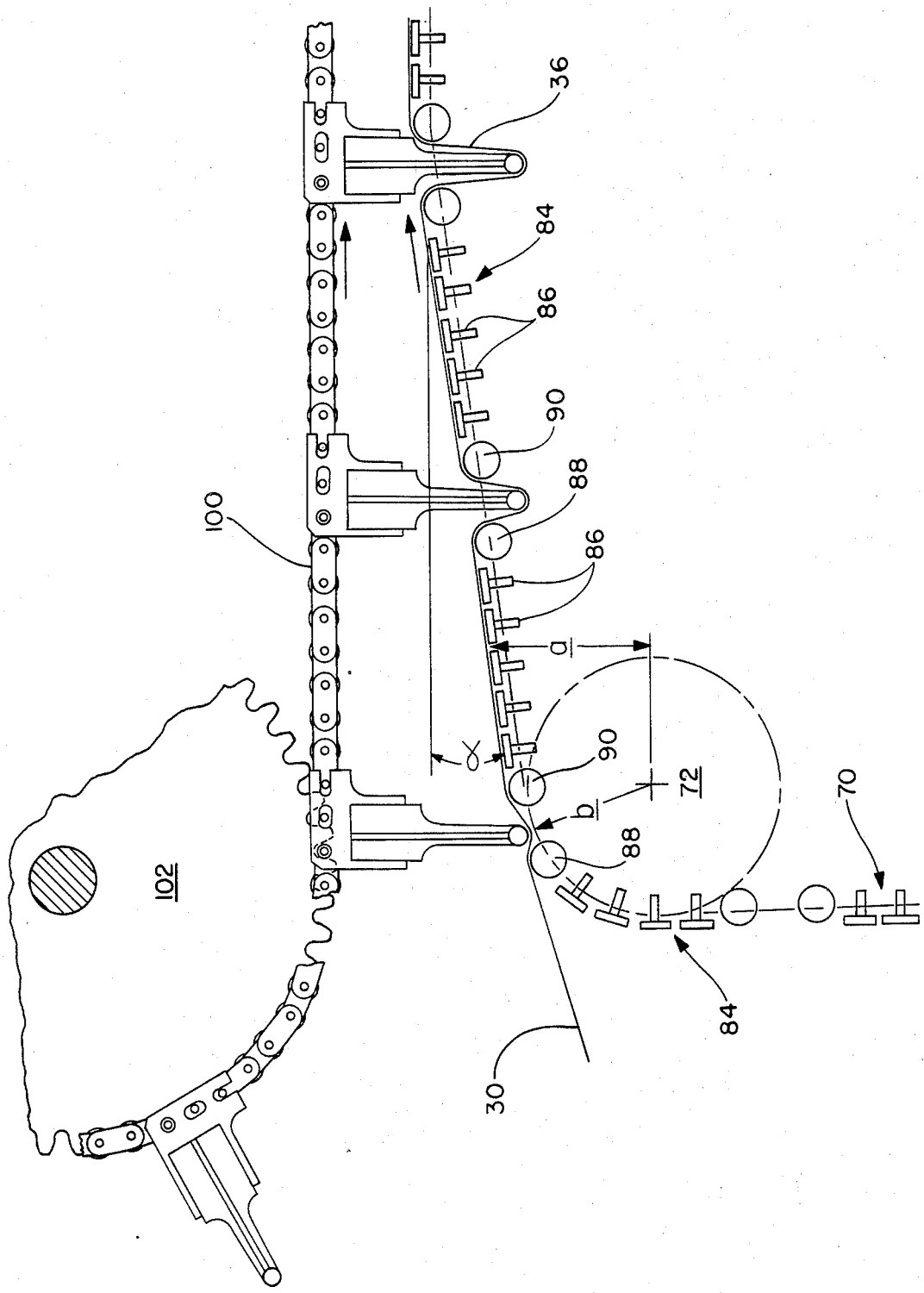
FIG. 4 is a simplified side elevation, cross-sectional view showing the feed end of the apparatus illustrated in FIG. 3.
Figure 5:
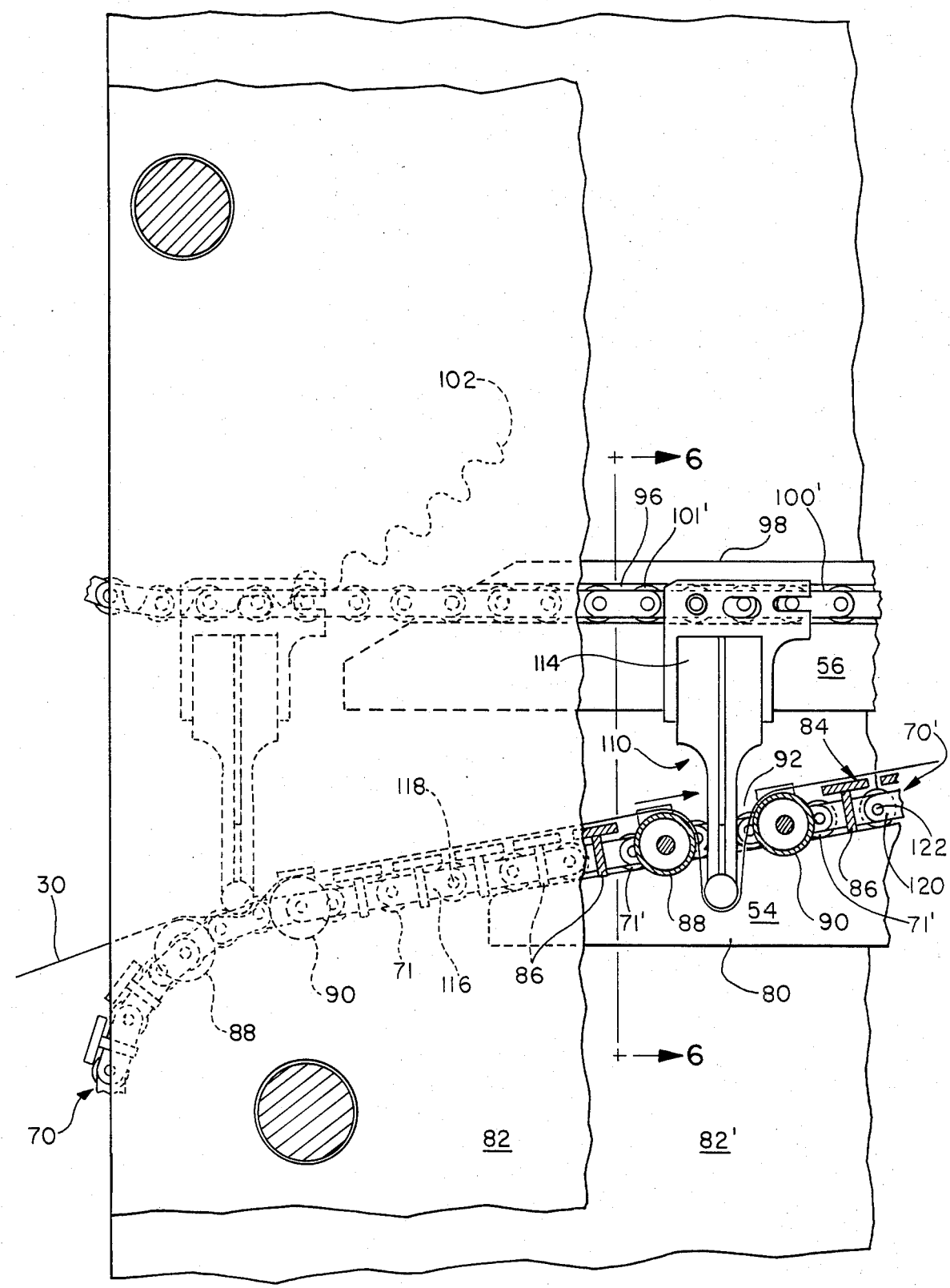
FIG. 5 is a side elevation, partially broken away side elevation view at the feed end of the apparatus shown in FIG. 3.

As shown in FIGS. 3-6, the first conveyor means 54 comprises a pair of endless conveyor chains 70, 70' of a well known variety on each side of the first conveyor means 54. The chains 70, 70' rotate together in a clockwise direction relative to the views of FIGS. 3-5. The chain 70 is trained around idler sprockets 78 and 72 at the feed end of the apparatus and around drive sprocket 74 and idler sprocket 76 at the exit end. Chain 70' is similarly arranged around drive and idler sprockets which are not shown. As shown in FIG. 5, the chains 70 and 70' respectively include rollers 71 and chain links 116 connected together by pins 118. The chain 70' includes rollers 71' and chain links 120 connected together by pins 122. The rollers 71, 71' ride on guide means 80 and 80' respectively mounted on side plates 82 and 82'. Affixed to and carried by the conveyor chains 70 and 70' are a plurality of groups 84 of T-bars 86 which form a support surface for the web 30 on the first conveyor means 54. Each T-bar is affixed at one of the opposite ends to a chain 70 or 70'. Between each of the T-bar groups 84 are a pair of rollers 88 and 90 which define slots or gaps 92 into which the web 30 is tucked by the second conveyor means 56.

The second conveyor means 56 includes a pair of endless conveyor chains 100 and 100' which move in a counterclockwise direction relative to the views of FIGS. 3-5 and in generally the same direction as the chains 70 and 70' of the first conveyor means 54 through the tucking section 40, the elastic supply and application section 42, the ribbon cutting section 44, and the untucking section 46. The chains 100 and 100' are of a well known link type and the chain 100 is trained around a drive sprocket 108 and idler sprockets 102, 104 and 106. Chain 100' is similarly arranged around drive and idler sprockets which are not shown. The chains 100 and 100' respectively include rollers 101 and 101' which respectively ride in grooves 96, 96' on guide means 98 and 98'. The guide means 98 and 98' are respectively mounted on side plates 82, 82'. A plurality of tucker bar means 110 are respectively rigidly affixed at spaced apart intervals to the second conveyor chains 100 and 100'. The tucker bar means 110 includes a tucker bar 112 and support bracket means 114 and 114' attached to opposite ends of the tucker bar 112.

With reference to the first conveyor means 54 as shown in FIGS. 3-5, the guide means 80 and 80' are inclined toward the second conveyor means 56 at the feed end of the apparatus to thereby position the gaps 92 of the first conveyor means 54 such that the tucker bars 112 of the tucker bar means 110 gradually move into and also within the gaps 92 and form tucks 36 in the web 30. The first conveyor means 54 and its gaps 92 thus follow a path which converges with the path of the bars 112 of the tucker bar means 110. In FIG. 4, the angle of convergence is identified by the letter α. The convergence angle α may vary, with the maximum extent being determined by the amount of stress the web will withstand during a relatively fast tucking speed and web travel and the amount of disturbance to smooth, consistent operation the process will tolerate from the tucking operation. The exact value of α, within permissible operating limits, depends on the diaper size being manufactured and for this purpose may range from 5° to 10°. The guide means 80 and 80' thus provide an inclined path that the first conveyor means 54 follows such that the distance a, as shown in FIG. 4, between the inclined path and a plane through the axis of the sprocket 72 and parallel to the direction of the second conveyor means 56 opposite the inclined path of the first conveyor means 54, in a direction perpendicular to the plane, is larger than the radius b of the sprocket 72. It should be noted that, although it is preferable that the first conveyor means 54 be inclined toward the second conveyor means 56 so that the gaps 92 move into the path of the tucker bars 112, it is possible to utilize guide means to incline the second conveyor means 56 or both of the conveyor means to accomplish the desired tucking operation. In the context of this invention, then, the term "incline" and forms thereof means that the first and second conveyor means and in particular their respective conveyor chains or belts as well as the gaps or tucker bars carried by the conveyor means, follow paths at an angle relative to each other.

Rather than move the tucker bars 112 into the gaps 92 while the first conveyor means 54 is moving along the angular portion of its path under the guidance of means 80 and 80', the tucker bars 112 may be moved into the gaps 92 while the first conveyor means 54 and the gaps 92 are moving along the angular arcuate portion of their path following the periphery of the sprocket 72. The benefit of moving the bars 112 into the gaps 92 at this point in the path of the latter is that deeper tucks 36 can be easily formed thereby where this is necessary for the size or type of diaper being fabricated. The rollers 88 and 90 are mounted on and pivot with the chain links 116 and 120 as the links 116 move along the periphery of the sprocket 72 and the links 120 move along the periphery of a corresponding sprocket. This will cause the outward extremities, relative to the axis of the sprocket 72, of the rollers 88 and 90 to move away from each other and thereby present wider gaps 92 for the tucker bars 112 to enter. This is an additional advantage to beginning the tucking step while the gaps 92 are moving along the periphery of the sprocket 92.

The inclination of the first conveyor means 54 toward and away from the second conveyor means 56 at the respective feed and exit ends of the apparatus requires the first conveyor means 54 to move a greater distance during this portion of its travel than the second conveyor means 56. Since the two conveyor means are traveling at the same speed to maintain registry of the tucker bar means 110 and the gaps 92, the greater travel distance of the first conveyor means results in the tucker bars 112 advancing within the gaps 92, during travel from the feed end to the exit end of the apparatus, from an initial position relatively adjacent the feed end of the apparatus to a position relatively remote from the feed end and adjacent the exit end of the apparatus.

Considering again the insertion of the tucker bar means into the gaps 92, as the first and second conveyor means move opposite each other and in the same direction, each of the tucker bar means 110 is opposite and in registry with the gap 92. Thus, as the two conveyor means move toward each other the tucker bar means 110 are gradually inserted into the gaps 92. While the tucker bar means 110 are inserted into the gaps 92, the tucker bar means 110 are maintained in a single angular position by the chains 100, 100' so that the problems of insertion of the tucker bar means 110 into the gaps 92 is minimized and there is no bumping or scuffing of the tucker bar means 110 and the web 30 against the rollers 88 and 90. The first and second conveyor means move toward each other at first and second rates, respectively, which may be the same or different depending on the amount of inclination of each of the two conveyors toward each other.

After the maximum insertion of the tucker bar means 110 into the gaps 92 so that the forming of the tucks 36 is completed, the elastic ribbons 34 are applied to the web 30 and the ribbons 34 are cut by the cutter 64 opposite the tucks 36 to form discrete, spaced elastic strips 22 and 24 extending in a direction parallel to the length of the web 30. The conveyor chains 70, 70' and the gaps 92 are then guided in a direction diverging from the second conveyor means 56 by the inclination of the guide means 80, 80' away from the second conveyor means 56. The conveyor chains 70 and 70' then follow a path along the perimeter of the idler sprockets at the exit end of the apparatus and return to the feed end of the apparatus around the perimeter of the idler sprockets at the feed end of the apparatus.

An apparatus and a method is thus provided for elasticizing only the leg areas of a disposable diaper by tucking the web from which the diaper is formed at appropriate locations along the length of the web and bonding elastic to the web across the tucks. The tucked portion of the web, after cutting of the elastic ribbon opposite the tucked portion, constitutes the waist area of the finished diaper.

It will be understood that the foregoing description of the present invention is for purposes of illustration only and that the invention is susceptible of a number of modifications or changes, none of which entail any departure from the spirit and scope of the present invention as defined in the hereto appended claims.

What is claimed is:

1. In an apparatus for applying elastic ribbon to spaced apart areas of a continuously moving web, said apparatus having a feed end at which the web is fed to the apparatus and an exit end at which the web and elastic leave the apparatus, the combination comprising:
   first conveyor means onto which the web is fed including web supporting means engaging the web and having spaced apart gaps therein;
   a plurality of tucker bar means;
   second conveyor means for carrying the tucker bar means through the apparatus and moving the tucker bar means and spaced portions of the web into said gaps to form tucks in the web;
   guide means for positioning the gaps of the first conveyor to permit gradual movement of the tucker bar means in the gaps and forming of the tucks;
   each tucker bar means has a position, at the feed end of the apparatus, in that portion of the gap most adjacent said feed end and advances to a position, while moving through said apparatus, in that portion of the gap most adjacent said exit end;
   means for moving the elastic ribon to a position spanning said tucks and in engagment with the spaced apart areas of the web; and
   means for adhering the elastic ribbon to the web.

2. The apparatus according to claim 1 wherein each tucker bar means is rigidly affixed to the second conveyor means and has a single angular position while disposed within one of said gaps.

3. The apparatus according to claim 1 wherein the guide means converges toward the second conveyor means at an angle in the range of 5° to 10°.

4. The apparatus according to claim 1 further comprising:
   circular sprocket means rotatably supporting the first conveyor means; and wherein
   the first conveyor means has a circular path around the sprocket means and moves said gaps along said circular path; and
   the second conveyor means and the tucker bar means have a straight line path intersecting the circular path of the gaps along which the second conveyor means moves the tucker bar means into the gaps.

5. The apparatus according to claim 4 wherein each tucker bar means is rigidly affixed to the second conveyor means and has a single angular position while disposed within one of said gaps.

6. A method for applying elastic strip material to spaced apart areas of a continuously moving web comprising the steps of:
   feeding the web at a feed station onto a first conveyor having gaps in a supporting surface to support the web between the gaps;
   moving a seocnd conveyor carrying a plurality of tucker bars in registry with said gaps in the same direction as that of the first conveyor;
   while moving the first and second conveyors in the same direction, moving them toward each other to insert each tucker bar into a portion of a gap most adjacent the feed station and form tucks in the web;
   advancing the tucker bar while it moves with the second conveyor from a portion of the gap most adjacent the feed station to a portion of the gap most remote from the feed station; and
   moving the elastic strip material continuously into engagement with the spaced apart areas of the web and spanning said tucks.

7. In an apparatus for applying elastic ribbon to a continuously moving web having alternating leg and waist areas corresponding to the leg and waist areas of a disposable diaper, the combination comprising:
   a feed end on said apparatus at which the web is fed to the apparatus;
   first conveyor means including web supporting means engaging the web and having spaced apart gaps therein;
   a plurality of tucker bar means;
   second conveyor means upon which the tucker bar means are mounted for moving each tucker bar means and a waist area of the web into a gap to form tucks in each of the waist areas of the web having a depth substantially equal to the length of a diaper waist area between leg areas, each tucker bar means having a position, upon initially moving into a gap, in that portion of the gap most adjacent said feed end and subsequently advancing to a position in that portion of the gap most remote from said feed end;
   guide means for positioning the gaps of the first conveyor means to permit gradual movement of the tucker bar means into the gaps and forming of the tucks, said guide means converging toward the second conveyor means at an angle in the range of 5° to 10° and a distance such that the extension of each tucker bar means through a gap equals said depth of a tuck;
   means for moving the elastic ribbon to a position spanning said tucks and in engagement with the leg areas of the web; and
   means for adhering the elastic ribbon to the web.

8. A method for applying elastic strip material to a continuously moving web having alternating leg and waist areas corresponding to the leg and waist areas of a disposable diaper comprising the steps of:
   feeding the web at a feed station onto a moving first conveyor means having gaps in a supporting surface and supporting the web between the gaps;
   moving a second conveyor means having a continuous conveyor chain trained on a rotating support means and carrying a plurality of tucker bars in registry with said gaps in the same direction as that of the first conveyor means;
   while moving the first and second conveyor means in the same direction and after the conveyor chain of the second conveyor means leaves the rotating support means, moving the first conveyor means toward the second conveyor means at a convergence angle not exceeding 10° to move each tucker bar against the waist area of the web through a gap a depth substantially equal to the length of a diaper waist area between leg areas to form a tuck in the waist area;
   while converging the second conveyor means toward the first conveyor means, advancing each tucker bar from a portion of the gap most adjacent feed station to a portion of the gap most remote from the feed station;
   moving elastic strip material to a position spanning each of said tucks and in engagement with the leg areas of the web; and
   adhering the elastic ribbon to the leg areas of the web.

* * * * *